United States Patent [19]

Spurr

[11] Patent Number: 5,561,233
[45] Date of Patent: Oct. 1, 1996

[54] PROCESS FOR THE PREPARATION OF AN INTERMEDIATE OF A BENZO[A]QUINOLIZINONE DERIVATIVE

[75] Inventor: Paul Spurr, Riehen, Switzerland

[73] Assignee: Hoffmann-La Roche Inc., Nutley, N.J.

[21] Appl. No.: 452,793

[22] Filed: May 30, 1995

Related U.S. Application Data

[62] Division of Ser. No. 327,159, Oct. 21, 1994.

[30] Foreign Application Priority Data

Oct. 28, 1993 [CH] Switzerland .................. 3252/93

[51] Int. Cl.⁶ .................................................. C07D 455/06
[52] U.S. Cl. .................................................. 546/95
[58] Field of Search .............................. 546/95; 514/294

[56] References Cited

U.S. PATENT DOCUMENTS

| | | | |
|---|---|---|---|
| 4,735,940 | 4/1988 | Fischer et al. | 514/212 |
| 4,889,848 | 12/1989 | Fischer et al. | 514/212 |
| 5,026,892 | 6/1991 | Kirchhoff | 556/419 |
| 5,036,066 | 7/1991 | Fischer et al. | 514/211 |
| 5,281,711 | 1/1994 | Scherschlict et al. | 546/95 |
| 5,321,021 | 6/1994 | Fischer et al. | 514/211 |
| 5,326,769 | 7/1994 | Scherschlict et al. | 514/294 |

FOREIGN PATENT DOCUMENTS

| | | |
|---|---|---|
| 0183994 | 6/1986 | European Pat. Off. |
| 0496274 | 1/1992 | European Pat. Off. |
| 650966 | 5/1995 | European Pat. Off. |

OTHER PUBLICATIONS

Spurr, PR, Tetrahedron Lett. (1995). 36(16) 2745–8.
Fischer, et al. Helvetica Chimica Acta, vol. 73, pp. 763–781 (1990).
Larsen, et al. J. Org. Chem. vol. 56, pp. 6034–6038 (1991).
Bhat, et al. Synthetic Communications, vol. 15(7) pp. 587–598 (1985).
Tamazawa et al., J. Med. Chem. vol. 29, pp. 2504–2511 (1986).

*Primary Examiner*—C. Warren Ivy
*Assistant Examiner*—Evelyn Huang
*Attorney, Agent, or Firm*—George W. Johnston; Ellen Ciambrone Coletti

[57] ABSTRACT

The invention is concerned with a process for the preparation of a benzo[a]quinolizinone derivative of the formula

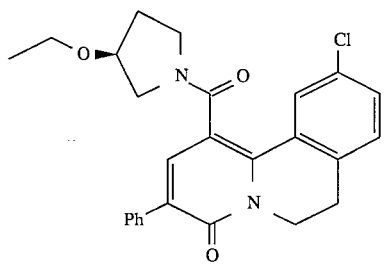

by reacting a compound of the formula

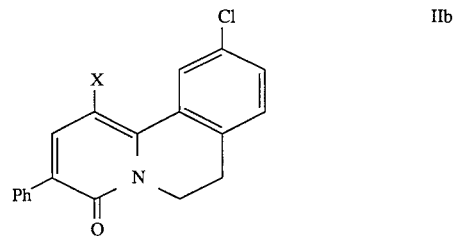

wherein X is halogen and Ph is phenyl, with carbon monoxide in the presence of a carbonylation catalyst and in the presence of (S)-3-ethoxypyrrolidine or a lower alkanol or water; where a lower alkyl ester of the 10-chloro-6,7-dihydro-4 -oxo-3-phenyl-4H-benzo[a]quinolizine-1-carboxylic acid has been obtained, converting this into the corresponding free acid; and, where the 10-chloro-6,7-dihydro-4-oxo-3-phenyl-4H-benzo[a]quinolizine-1-carboxylic acid has been obtained, reacting a reactive derivative thereof with (S)-3-ethoxypyrrolidine. The compound of formula I is useful for the treatment or prophylaxis of sleep disorders.

7 Claims, No Drawings

5,561,233

PROCESS FOR THE PREPARATION OF AN INTERMEDIATE OF A BENZO[A]QUINOLIZINONE DERIVATIVE

This is a division of application Ser. No. 08/327,159, filed Oct. 21, 1994.

BRIEF DESCRIPTION OF THE INVENTION

The invention relates to a process for the preparation of a benzo[a]quinolizinone derivative of the formula

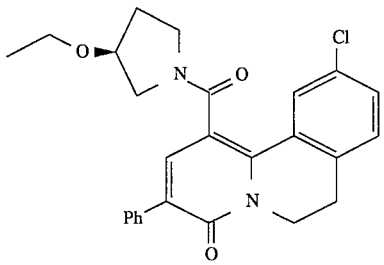

wherein Ph is phenyl.

The compound of formula I has valuable pharmacological properties. Since it has primarily a non-sedating, hypnotic and sleep-promoting activity, it can be used for the treatment or prophylaxis of illnesses, especially for the treatment of sleep disorders.

DETAILED DESCRIPTION OF THE INVENTION

As used herein, the term "lower alkyl" denotes a straight or branched-chain alkyl group containing 1 to 4 carbon atoms, for example, methyl, ethyl, propyl, isopropyl, butyl, t-butyl and the like. The term "lower alkanol" preferably denotes a straight or branched-chain alkanol containing 1 to 4 carbon atoms, for example, methanol, ethanol, propanol, isopropanol, butanol, t-butanol and the like. The term "halogen" denotes bromine, chlorine and iodine, preferably, bromine.

The preparation of compound I, the preparation of the intermediates, as well as, the intermediates of the formulas

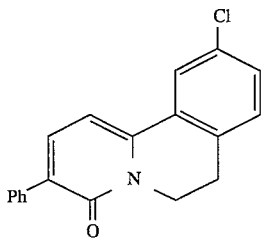 IIa and

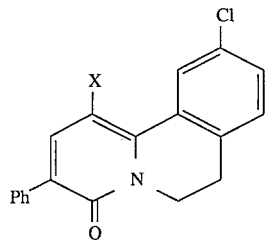 IIb wherein X is halogen and Ph is phenyl, are objects of the present invention.

The compound of formula I, its racemate as well as the pharmacological properties are known: see EP No. 183 994 and No. 496 274 which correspond to U.S. Pat. Nos. 4,735,940 and 5,281,711, respectively.

The benzo[a]quinolizinone derivative of formula I can be prepared in accordance with the invention by reacting a compound of the formula

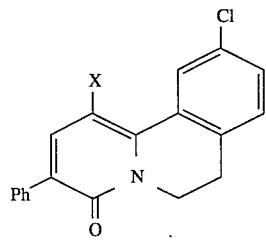 IIb wherein X is halogen and Ph is phenyl, with carbon monoxide in the presence of a carbonylation catalyst and in the presence of (S)-3-ethoxypyrrolidine or a lower alkanol or water; where a lower alkyl ester of the 10-chloro-6,7-dihydro-4-oxo-3-phenyl-4H-benzo[a]quinolizine-1-carboxylic acid has been obtained, converting the resulting ester into the corresponding free acid; and, where the 10-chloro-6,7-dihydro-4-oxo-3-phenyl-4H-benzo [a]quinolizine-1-carboxylic acid has been obtained, reacting a reactive derivative of formula XI with (S)-3-ethoxypyrrolidine in a known manner.

These preparation variants are shown in Scheme 1:

Scheme 1

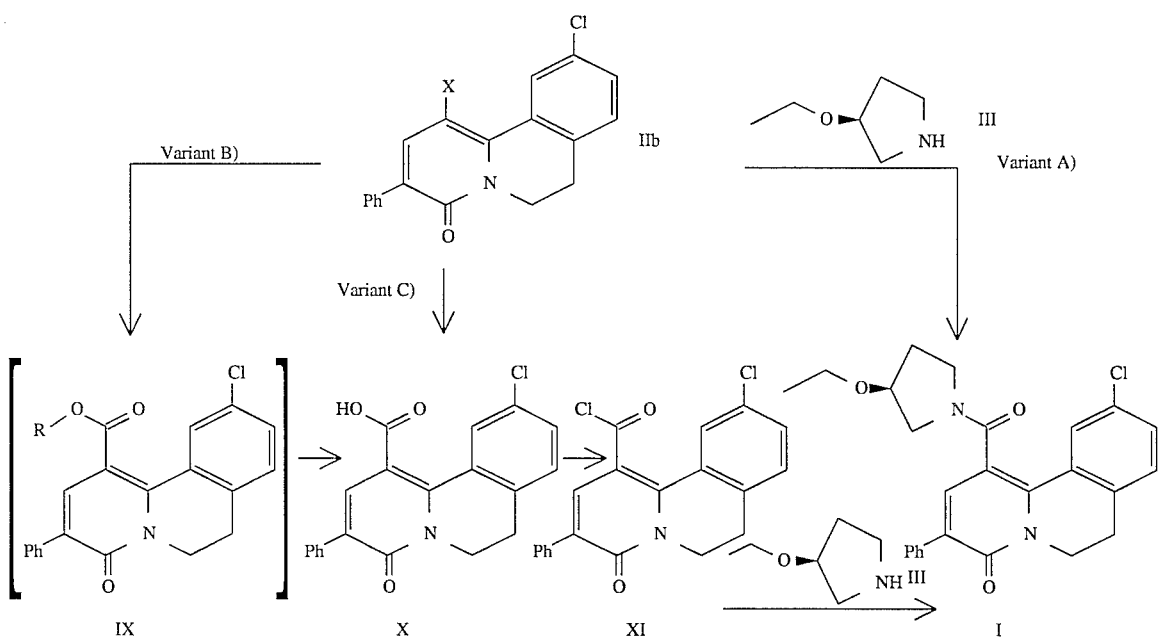

wherein X is halogen, R is lower alkyl and Ph is phenyl.

The following procedure can conveniently be used for the preparation of compound I according to process variant A), with X in the following description signifying bromine, chlorine or iodine.

1-Bromo-10-chloro-4-oxo-3-phenyl-6,7-dihydro-4H-benzo[a]quinoline (IIb where X=Br), $K_2CO_3$ and the pyrrolidine of formula III are suspended in a solvent. Acetonitrile or pyridine is, for example, suitable as the solvent. Subsequently, the suspension is treated with a catalyst and with 1,3-bis(diphenylphosphine)propane. Palladium acetate can conveniently be used as the carbonylation catalyst. The reaction is carried out in an autoclave, which is sealed air-tight, under vacuum conditions. The autoclave is then de-gassed with argon and charged with about 15 bar of carbon monoxide. The suspension is stirred at about 100° C. for several hours and the product is subsequently purified and dried.

According to process variant B) the preparation of compound I is carried out over several steps, whereby the ester IX need not be isolated. The following procedure can conveniently be used:

The compound IIb where X=Br, Cl or I is dissolved in an alcohol, for example, methanol, treated with a carbonylation catalyst, such as, for example, palladium acetate, and, after the addition of a base such as $KHCO_3$ or potassium acetate and 1,3-bis(diphenylphosphine)propane, reacted at about 90° C. for several hours in an autoclave which is charged with 4–8 bar of carbon monoxide.

The resulting ester of formula IX is then hydrolyzed to the corresponding acid of formula X with a dilute alkali, for example, with potassium hydroxide. The resulting acid is converted, for example, with oxalyl chloride in the presence of dimethylaminopyridine in ethyl acetate into the corresponding acid chloride of formula XI. This reactive derivative of formula XI can thereafter be converted into compound I with 3-ethoxypyrrolidine (III) or its hydrochloride in the presence of triethylamine.

Variant C) of Scheme 1 is a further possibility for the preparation of compound I. In this case, the halogen leaving group is replaced by an acid group in one step. The following procedure is conveniently used:

The compound of formula IIb in which X preferably is bromine is dissolved in a solvent, for example, dimethyl sulfoxide, treated with water, a carbonylation catalyst, for example, palladium acetate, as well as with 1,3-bis(diphenylphosphine)propane and with a base, for example, potassium carbonate.

The reaction is carried out in an autoclave, which is sealed air-tight, under a CO atmosphere of about 15 bar. The suspension is stirred at about 100° C. for several hours. Subsequently, the resulting acid is converted with oxalyl chloride in the presence of dimethylaminopyridine in ethyl acetate into the corresponding acid chloride of formula XI. This reactive derivative of formula XI can be converted as before into compound I with 3-ethoxypyrrolidine (III) or its hydrochloride in the presence of triethylamine.

The compound III used as the starting material is known (EP No. 496 274), which corresponds to U.S. Pat. No. 5,281,711, and can be prepared, for example, by alkylating (S)-1-benzyl-3-pyrrolidinol with an ethyl halide, such as ethyl bromide or ethyl iodide, in the presence of a base and subsequently cleaving off the benzyl group by catalytic hydrogenolysis. (S)-1-Benzyl-3-pyrrolidinol is a compound described in the literature; see. J. Med. Chem. 29, 2504–2511 (1986) and Synth. Comm. 15, 587–598 (1985) and is commercially available.

The compounds of formulas IIa and IIb are novel and can be prepared according to Scheme 2:

Scheme 2

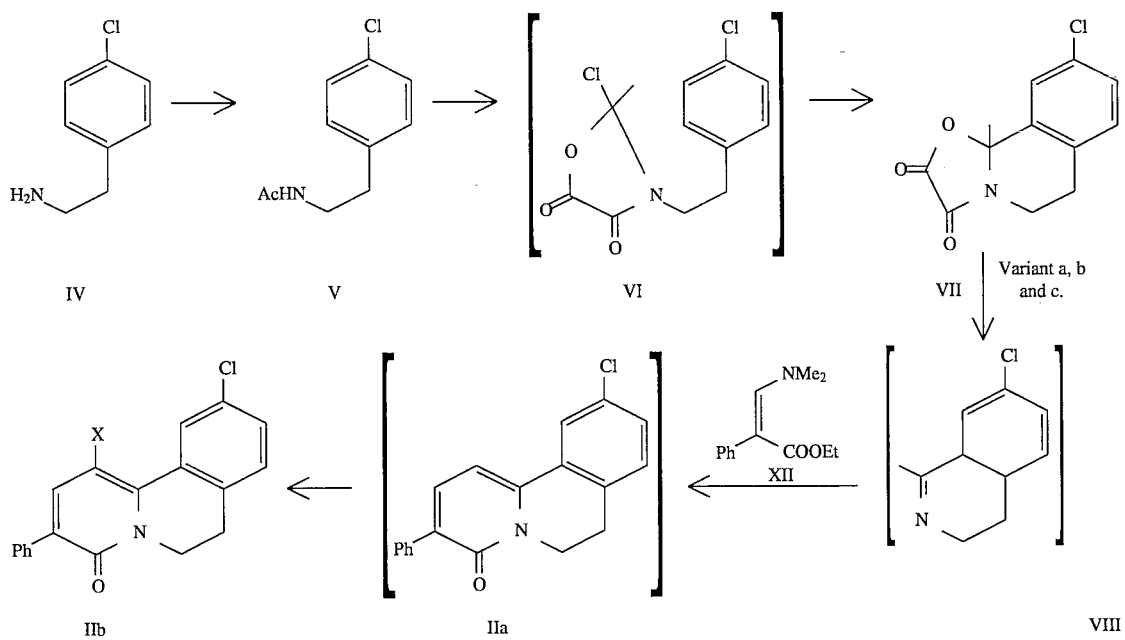

wherein X is halogen, Ac is acetyl, Me is methyl, Et is ethyl and Ph is phenyl.

The following procedure, as set forth in scheme 2, is conveniently used for the preparation of the compounds IIa and IIb, respectively.

The acylation of compound IV can be carried out with acetic anhydride. Toluene is the especially suitable solvent for this exothermic reaction, which is carried out at room temperature. The acetic acid which occurs as a byproduct during the acylation can be removed subsequently by azeotropic distillation. Amide V can also be prepared by amidating amine IV with methyl formate, ethyl acetate or isopropyl acetate.

The resulting compound V is, after reaction with oxalyl chloride in dichloromethane at room temperature, converted into intermediate VI. This can be converted, without isolation, into compound VII in the presence of a Lewis acid, preferably, the combination $FeCl_3/CH_2Cl_2$. However, the following Lewis acids are also practicable: $BF_3 \cdot (OCH_2CH_3)_2$, $AlCl_3$, $TiCl_4$ or $SnCl_4$ (J. Org. Chem., 56, 6034 [1991]).

The conversion of compound VII into compound IIa can be carried out in different ways. A thermolysis of compound VII with acetic acid at temperatures between 100°–120° C. to dihydroisoquinolines of formula VIII has been found to be convenient. This compound need not be isolated prior to the further reaction. The ring-closure, which has not been described in the literature, of is compound VIII with an aminoacrylate of formula XII is conveniently carried out in a polar, acidic medium which is suitable simultaneously as the catalyst and as the solvent, for example in glacial acetic acid at about 100° C. A successful reaction is, however, also possible in a polar, neutral medium such as dimethyl formamide at elevated temperatures. The reactions take a few hours and compound IIa is isolated in yields of 70 to 80%.

A further possibility for the preparation of compound IIa starting from the compound of formula VII comprises treatment with concentrated sulfuric acid in refluxing methanol, subsequent isolation of dihydroisoquinoline (VIII) and reaction with the aminoacrylate of formula XII, which can be carried out as described above.

Alternately, all reaction partners can be used simultaneously. In this case, the compound of formula VII is treated with the aminoacrylate of formula XII. Acetic acid is conveniently used as the solvent. The mixture is stirred for several hours, the reaction temperature being about 100° C. Subsequently, the resulting compound IIa can be halogenated with or without isolation.

Bromine is the most suitable leaving group for the preparation of compound I. Accordingly, one possible bromination variant is described in more detail hereinafter:

Compound IIa, which is in solution or isolated, is conveniently treated with a halogenating agent, preferably N-Bromosuccinimide. Acetic acid, $CH_2Cl_2$ or $CH_3CN$ can be used as the solvent. The bromination is carried out at temperatures between room temperature and 95° C. The yield of compound IIb is quantitative.

The presence of byproducts, which result from the reaction of the compounds of formula VIII and XII, has no influence on the course of the bromination. The bromo compound of formula II precipitates upon cooling to room temperature by the addition of water to the hot reaction solution. The oily byproducts remain in solution. The process in accordance with the invention, including the described process variants, permit the pharmacologically active compound of formula I to be obtained in yields which are about three times as high as in the known process described in Helv. Chim. Acta 73, 763 (1990).

This was not to be expected having regard to the many process steps, which are carried out in part without isolation of the intermediates formed.

A further advantage of the novel process is that the intermediate steps involving the formation of isomers or of an isothiocyanate, which render a process uneconomical on ecological and toxicological grounds, are not required.

The following Examples illustrate the present invention in more detail. They are, however, not intended to limit its scope in any manner. All temperatures are given in degrees Celsius.

1. Preparation of the intermediates of formulas IIa and IIb a) 2-(4-Chlorophenyl)-ethylacetamide (V)

155.6 g (1 mol) of 2-(4-chlorophenyl)-ethylamine (IV) were dissolved in 500 ml of toluene and treated with 107.2 g (1.05 mol) of acetic anhydride within 0.5 hour. The mixture was subsequently stirred at 80° for 0.25 hour. The solution was concentrated, taken up in 250 ml of toluene and, after drying at 40°/0.1 mbar/1.5 h., there was obtained an oil which slowly became solid.

Yield: quantitative, m.p. 93°–94° (toluene/hexane).

b) (R,S)-9-Chloro-10β-methyl-2,3,6,10β-tetrahydro-5H-oxazolo[2,3-α]isoquinoline-2,3-dione (VII)

204.9 g (1 mol) of 2-(4-chlorophenyl)-ethylacetamide (V) were dissolved in 2000 ml of dichloromethane and treated with 94.5 ml (1.1 mol) of oxalyl chloride within 0.75 hour. The solution was stirred at 30° for a further 0.5 hour and subsequently cooled to 5°. Thereafter, the solution was treated portionwise with 194.7 g (1.2 mol) of $FeCl_3$-within 0.5 hour,-whereby the temperature rose to 25°. The mixture was stirred at this temperature for 16 hours. The resulting black suspension was subsequently treated with 1000 ml of 4N HCl and stirred for a further 1 hour. The organic phase was then separated and washed once with 500 ml of water. The aqueous phase was extracted twice with 500 ml of dichloromethane each time. The organic extracts were combined and concentrated. There was obtained a pale brown solid.

Yield: 96%, m.p. 169° ($CH_2Cl_2$, dec. to (VIII)).

As an alternative for the working-up, the solvent can be evaporated after treatment of the reaction mixture with HCl. The separated product is filtered off and washed several times with water.

Variant a) for the preparation of the compound of formula IIb.

c) 7-Chloro-3,4-dihydro-1-methylisoquinoline (VIII)

A solution of 248.1 g (1.0 mol) of (R,S)-9-chloro-10β-methyl -2,3,6,10β-tetrahydro-5H-oxazolo[2,3-α]isoquinoline-2,3-dione (VII) and 2000 ml of methanol was treated with 150 ml (2.8 mol) of concentrated sulfuric acid within 0.5 hour. In so doing the temperature rose to about 45°. Subsequently, the brown suspension was boiled at reflux for 24 hours until the solution took on a clear dark brown color. Afterwards, the solvent was concentrated and treated with 1000 ml of water. The aqueous solution was extracted three times with a total of 1500 ml of ethyl acetate and the combined organic extracts were washed twice with 250 ml of water. The aqueous phases were combined and adjusted to pH 9 with 500 ml of 25% $NH_4OH$. The oily upper phase was extracted three times with 500 ml of dichloromethane. The combined organic phases were washed twice with 250 ml of water and filtered. The filtrate was concentrated and there was obtained a dark yellow-green oil which was dried at 45°/0.1 mbar.

Yield: 164.7 g, 92%. Platelets with m.p. 40°–42° formed after a while.

d) 10-Chloro-4-oxo-3-phenyl-6,7-dihydro-4H-benzo[a]quinoline (IIa)

89.8 g (0.5 mol) of 7-chloro-3,4-dihydro-1-methyl-isoquinoline (VIII) and 115.1 g (0.525 mol) of ethyl E/Z-2-phenyl-3-(dimethylamino)acrylate were dissolved in 600 ml of glacial acetic acid and heated to 95° (oil bath) within 0.33 hour. The mixture was subsequently stirred for 3 hours. A dark brown solution was obtained.

e) 1-Bromo-10-chloro-4-oxo-3-phenyl-6,7-dihydro-4H-benzo[a]quinoline (IIb)

The solution prepared in Example 1 d) was treated with 111.2 g (0.625 mol) of N-bromosuccinimide at 90° and stirred for 1 hour while heating. Crystallization of the desired product was carried out by the addition of 150 ml of water. The mixture was cooled to 20° within 0.75 hour and subsequently stirred for a further 0.5 hour. The separated product was filtered off and subsequently washed with 200 ml of a solution consisting of acetic acid and water in the ratio of 1:1 and three times with cold t-butyl methyl ether. The bromide was obtained as a yellow crystalline solid after drying (60°/40mbar/4h). Yield: 138.5 g=72%, m.p. 196°–197° (acetic acid/$H_2O$).

Variant b) for the preparation of the compound of formula IIb.

1-Bromo-10-chloro-4-oxo-3-phenyl-6,7-dihydro-4H-benzo[a]quinoline (IIb)

A solution of 5.03 g (20 mmol) of (R,S)-9-chloro-10β-methyl -2,3,6,10β-tetrahydro-5H-oxazolo[2,3-α]isoquinoline-2,3-dione (VII) and 4.40 g (20 mmol) of ethyl E/Z-2-phenyl-3-(dimethylamino)acrylate (XII) in 25 ml of acetic acid was stirred at 100° for 4 hours. Without isolating the resulting compound, 10-chloro-4-oxo-3 -phenyl-6,7-dihydro-4H-benzo[a]quinoline (IIa), this solution was treated portionwise with 4.45 g ,(25 mmol) of N-bromosuccinimide within 0.25 hour and the resulting brown reaction solution was subsequently stirred at 100° for 1 hour.

The compound crystallized in yellow needles after adding 5 ml of water and cooling the reaction mixture to room temperature. The residue was filtered off and the product was washed twice with 10 ml of aqueous acetic acid (1:1) each time and once with 5 ml of t-butyl methyl ether. The yield was 5.76 g (75%).

Variant c) for the preparation of the compound of formula IIb.

1-Bromo-10-chloro-4-oxo-3-phenyl-6,7-dihydro-4H-benzo[a]quinoline (IIb)

A solution of 5.03 g (20 mmol) of (R,S)-9-chloro-10β-methyl -2,3,6,10β-tetrahydro-5H-oxazolo[2,3-α]isoquinoline-2,3-dione (VII) in 25 ml of acetic acid was stirred at 120° for 4 hours. 7-Chloro -3,4-dihydro-1-methyl-isoquinoline resulted as the brown reaction solution (VIII). It was cooled to 100° and treated with 4.40 g (20 mmol) of ethyl E/Z-2-phenyl-3-(dimethylamino)acrylate (XII). Subsequently, it was stirred at 100° for 3 hours and the reaction solution was treated with 4.45 g (25 mmol) of N-bromo-succinimide. The addition was carried out portionwise within 0.25 hour. The mixture was subsequently stirred at 100° for 1 hour.

The compound crystallized out in yellow needles after adding 5 ml of water and cooling the reaction mixture to room temperature. The residue was filtered and the product was washed twice with 10 ml of aqueous acetic acid (1:1) and once with 5 ml of t-butyl methyl ether. The yield was 6.03 g (76%).

Preparation of
(S)-1-[(10-chloro-6,7-dihydro-4-oxo-3
-phenyl-4H-benzo[a]quinolizin-1-yl)carbonyl]-
3-ethoxypyrrolidine (I)

2.1.a) 10-Chloro-4-oxo-3-phenyl-6,7-dihydro-4H
-benzo[a]quinolizine-1-carboxylic acid (X) (variant
B)

A suspension of 38.67 g (100 mmol) of 1-bromo-10-chloro-4 -oxo-3-phenyl-6,7-dihydro-4H-benzo[a]quinoline (IIb) and 500 ml of methanol was treated in a glass autoclave with 0.011 g (0.05 mmol) of palladium acetate, 0.025 g (0.06 mmol) of 1,3-bis(diphenylphosphine)propane and with 20 g (200 mmol) of KHCO$_3$. The pressure in the autoclave was adjusted to 0.1 bar and de-gassification was carried out under an argon atmosphere. The de-gassification was repeated twice. At 0.1 bar the autoclave was charged with 4 bar of carbon monoxide. The suspension was stirred at 700 rpm for 20 hours at 90° (oil bath 100°). Subsequently, the clear yellow solution was cooled to 20°–25° and the excess carbon monoxide was discharged. A thick suspension of the ester IX resulted upon cooling and this was stirred and de-gassed a further three times. The reaction mixture was washed into a different apparatus with the aid of a solution of 14.0 g of KOH (0.25 mol) in 500 ml of water as well as 50 ml of methanol and boiled at 750 at reflux (oil bath 90°) for 4 hours. The olive-green solution was cooled to 50°, filtered through a Florosil pad and the residue was washed with 50 ml of methanol. The filtrate was concentrated and simultaneously replaced with 500 ml of water at 40°. The aqueous phase was washed twice with 250 ml of ethyl acetate each time and the combined aqueous phases were extracted with 1% KOH. The organic phase was discarded. The aqueous phase was cooled to 5° and adjusted to pH 1 with 40 ml of concentrated HCl. Thereafter, the mixture was stirred for 0.25 hour, the resulting acid was filtered and washed portionwise with 150 ml of water. The drying and isolation of the resulting white powder was carried out at 50°/0.1 mbar/7 h. Yield 98%, m.p. 285–286° (dec.).

2.1.b) (S)-1-[(10-Chloro-6,7-dihydro-4-oxo-
3-phenyl-4H -benzo[a]quinolizin-1-yl)carbonyl]-
3-ethoxypyrrolidine (I)

A suspension of 8.79 g (25 mmol) of 10-chloro-4-oxo-3 -phenyl-6,7-dihydro-4H-benzo[a]quinolizine-1-carboxylic acid (X) in 125 ml of ethyl acetate was-treated with 0.076 g (0.625 mmol) of dimethylaminopyridine and 3.49 g (27.5 mmol) of oxalyl chloride. The mixture was then stirred at 600 for 3 hours. The yellow solution (XI) was concentrated and the residue was taken up in 125 ml of toluene. This was treated either with 5.26 g (52 mmol) of triethylamine and 3.94 g (26mmol) of (S)-3-ethoxypyrrolidine hydrochloride or with 2.63 g (26 mmol) of triethylamine and 3.0 g (26 mmol) of (S)-3-ethoxypyrrolidine and stirred for 4 hours. Subsequently, the solution was washed in succession with 100 ml of water, 100 ml of 1N HCl, 100 ml of 0.5N KHCO$_3$ and then again with 100 ml of water. The individual aqueous phases were extracted with 100 ml of toluene and the combined organic extracts were dried with 20 g of Na$_2$SO$_4$.

The residue obtained after filtration and concentration was dried at 50°/0.1 mbar/2 h. Compound I was obtained in 85% yield, based on the acid, after purification by recrystallization from acetone/water and acetone/hexane. M.p. 133°–134°.

2.2 (Variant A)

A suspension of 3.86 g (10 mmol) of 1-bromo-10-chloro-4 -oxo-3-phenyl-6,7-dihydro-4H-benz[a]quinoline (IIb) in 25 ml of acetonitrile was treated in an autoclave with 1.21 g (10.5 mmol) of (S)-3-ethoxypyrrolidine (III), 0.022 g (0.1 mmol) of palladium acetate, 0.062 g (0.15 mmol) of 1,3-bis(diphenylphosphine)propane and 6.91 g (50 mmol) of potassium carbonate. The autoclave was sealed air-tight and adjusted to 0.1 bar. The stirring velocity was 700 rpm. The de-gassification procedure was repeated twice with argon then the pressure was again adjusted to 0.1 bar. The autoclave was subsequently charged with carbon monoxide to about 15 bar and the suspension was stirred at 100° for 24 hours. The CO pressure at this temperature was about 20 bar. The solution was cooled to a temperature of about 20° and the excess CO was discharged. The resulting yellow suspension was treated with 50 ml of ethyl acetate and 50 ml of water. The aqueous phase was separated and extracted with 25 ml of ethyl acetate. The combined organic phases were dried over sodium sulfate, filtered and concentrated. There was obtained a beige colored solid which was purified by chromatography (ethyl acetate/hexane). Yield: 3.98 g, 89%.

2.3 (Variant C)

A solution of 3.86 g (10 mmol) of 1-bromo-10-chloro-4-oxo -3-phenyl-6,7-dihydro-4H-benzo[a]quinoline (IIb) in 45 ml of dimethyl sulfoxide was treated with 5 ml of water, 0.022 g (0.1 mmol) of palladium acetate, 0.062 g (0.15 mmol) of 1,3-bis(diphenylphosphine)propane and 2.0 g (20 mmol) of KHCO$_3$ in an autoclave. The autoclave was sealed air-tight and adjusted to 0.1 bar. The stirring velocity was 700 rpm. The de-gassification procedure was repeated twice and the autoclave was again adjusted to 0.1 bar and charged with about 15 bar of carbon monoxide. The suspension was stirred at 100° for 20 hours. The CO pressure at this temperature was about 20 bar. The solution was subsequently cooled to a temperature of 20° and the excess CO was discharged. The resulting yellow suspension was treated with 0.6 g of NaOH in 150 ml of water, filtered and the filter residue was treated with 50 ml of water. The filtrate was washed three times with 50 ml of ethyl acetate each time. The washed and combined aqueous phases were cooled to 5° and adjusted to pH 1 with 5 ml of concentrated HCl. The resulting precipitate was filtered, washed twice with 50 ml of water and dried. Yield 3.17 g (90%).

Conversion to a compound of formula I was carried out as described in example 2.1b).

I claim:

1. A compound selected from the group consisting of compounds of the formulas:

wherein X is halogen and Ph is phenyl.

2. A compound according to claim 1, 10-Chloro-4-oxo-3-phenyl-6,7-dihydro-4H-benzo[a]quinoline.

3. A compound according to claim 1, 1-Bromo-10-chloro-4-oxo-3-phenyl-6,7-dihydro-4H-benzo[a]quinoline.

4. A process for the preparation of 10-Chloro-4-oxo-3-phenyl-6,7-dihydro-4H-benzo[a]quinoline, which process comprises reacting the compound of the formula:

VII with the compound of formula:

XII wherein Ph is phenyl, Et is ethyl and Me is methyl.

5. A process for the preparation of 10-Chloro-4-oxo-3-phenyl-6,7-dihydro-4H-benzo[a]quinoline, which process comprises hydrolyzing the compound of the formula:

VII to the compound of the formula:

VIII and reacting the compound of formula VIII with the compound of formula:

XII wherein Ph is phenyl, Et is ethyl and Me is methyl.

6. A process for the preparation of 1-Halo-10-chloro-4-oxo-3-phenyl-6,7-dihydro-4H-benzo[a]quinoline, which process comprises treating 10-Chloro-4-oxo-3-phenyl-6,7-dihydro-4H-benzo [a]quinoline with a halogenating agent.

7. A process according to claim 6, wherein the halogenating agent is N-Bromosuccinimide.

* * * * *